United States Patent [19]

Vago

[11] Patent Number: 5,921,102
[45] Date of Patent: Jul. 13, 1999

[54] STORAGE APPARATUS PARTICULARLY WITH AUTOMATIC INSERTION AND RETRIEVAL

[75] Inventor: Robert E. Vago, Northbrook, Ill.

[73] Assignee: Cryo-Cell International, Inc., Clearwater, Fla.

[21] Appl. No.: 08/828,402

[22] Filed: Mar. 28, 1997

[51] Int. Cl.$^6$ ............................ F25D 23/12; F25D 23/02; B65G 1/06
[52] U.S. Cl. ................................ 62/337; 62/266; 62/381; 62/51.1
[58] Field of Search ............................ 62/51.1, 62, 337, 62/381, 266

[56] References Cited

U.S. PATENT DOCUMENTS

| | | |
|---|---|---|
| 2,599,173 | 6/1952 | Hamilton . |
| 2,695,729 | 11/1954 | Hornish ................................. 62/381 X |
| 2,928,705 | 3/1960 | Goldsmith . |
| 3,004,408 | 10/1961 | Dros et al. ............................ 62/381 X |
| 3,034,845 | 5/1962 | Haumann . |
| 3,088,787 | 5/1963 | Perkins ................................. 62/381 X |
| 3,163,994 | 1/1965 | Haumann et al. ..................... 62/381 X |
| 3,456,817 | 7/1969 | Irazoqui . |
| 3,662,565 | 5/1972 | Gram . |
| 3,696,631 | 10/1972 | Valdes . |
| 3,782,133 | 1/1974 | Desperier et al. ......................... 62/381 |
| 3,787,699 | 1/1974 | Menachem et al. .................. 62/381 X |
| 4,245,483 | 1/1981 | Murai . |
| 4,340,263 | 7/1982 | Webb . |
| 4,870,829 | 10/1989 | Oullette et al. . |
| 4,969,336 | 11/1990 | Knippscheer et al. ................ 62/337 X |
| 5,125,240 | 6/1992 | Knippscheer et al. . |
| 5,176,202 | 1/1993 | Richard ................................ 62/337 X |
| 5,233,844 | 8/1993 | Knippscheer et al. . |
| 5,638,686 | 6/1997 | Coelho et al. ........................ 62/337 X |

FOREIGN PATENT DOCUMENTS

| | | |
|---|---|---|
| 40979/89 | 4/1990 | Australia . |
| 2421387 | 5/1974 | Germany . |

*Primary Examiner*—Christopher B. Kilner
*Attorney, Agent, or Firm*—Henry D. Coleman; R. Neil Sudol

[57] ABSTRACT

A storage unit includes a housing with a storage chamber, a carrier disposed inside the chamber for supporting a plurality of specimens in a predetermined array, and an access port on the housing for enabling access to the chamber for insertion and retrieval of specimens from the carrier. The access port includes an opening in the housing and a plug member removably located in the opening. The carrier is provided with a seat for receiving the plug member during an access operation, so that the plug member is located in the chamber during the access operation. A drive is operatively connected to the carrier for moving the carrier in the chamber to juxtapose different specimens to the access port. An insertion and removal mechanism is coupled to the housing for alternately inserting and removing specimens from the chamber via the access port during the access operation.

43 Claims, 11 Drawing Sheets

STORAGE APPARATUS PARTICULARLY WITH AUTOMATIC INSERTION AND RETRIEVAL

BACKGROUND OF THE INVENTION

This invention relates to a storage apparatus. More particularly, this invention relates to an apparatus with automatic insertion and retrieval of samples from a storage container. More specifically, this invention relates to an apparatus for the preservation of biological specimens at various temperatures, including but not limited to the temperature of liquid nitrogen. This invention also relates to an associated method for storing a multitude of samples, e.g., biological samples.

When properly treated, biological specimens can be stored almost indefinitely at temperatures approaching that of liquid nitrogen so long as that temperature is maintained. However, once the temperature of a specimen is raised, especially to a level where thawing occurs, the integrity of the specimen suffers if the specimen is then refrozen.

Many conventional cryogenic storage units are simple containers with removable racks having multiple shelves. Specimens are inserted and removed from the storage units manually through a door in the top of the unit. Retrieval operations always necessitate the removal of many specimens in the same rack as the desired specimen.

A considerable advance in the mass cryogenic storage of biological specimens was made with U.S. Pat. No. 4,969,336. That patent disclosed the automated moving of specimens along a predetermined path inside a storage tank, with automated insertion and retrieval operations under computerized tracking control.

A further significant improvement in the cryogenic storage arts was introduced with U.S. Pat. No. 5,233,844. That patent discloses a cryogenic storage unit comprising a plurality of independently rotatable storage shelves located one above the other in an insulated chamber. Each shelf supports several pie-slice-shaped trays each carrying a multiplicity of specimens in vials. The shelves each have a pie-slice-shaped opening, with these openings being disposed one above the other to define a vertical access path. To retrieve a particular vial or specimen from the storage unit, the shelf containing the desired specimen is rotated so that the tray containing the specimen is located in the access path. A lift mechanism raises the tray to the top of the unit where a robotic arm retrieves the desired specimen.

The cryogenic storage unit of U.S. Pat. No. 5,233,844, although superior to conventional cryogenic storage units which are manually operated, is subject to the disadvantage of having a significant number of moving parts. Such moving parts suffer from wear and thus require substantial repair and maintenance efforts.

Moreover, automated storage units pursuant to U.S. Pat. No. 5,233,844 suffer from the formation of ice at the access openings to the storage units. This problem is overcome in existing machines by the utilization of heating elements at the access openings. Heating, of course, militates against maintaining desired low temperatures in the storage units.

OBJECTS OF THE INVENTION

An object of the present invention is to provide an improved storage unit with automatic insertion and retrieval.

An additional object of the present invention is to provide such a storage unit which has reduced insertion and retrieval times.

A further object of the present invention is to provide an automatic storage device which is has a simpler construction than prior cryogenic storage devices.

Another object of the present invention is to provide a storage apparatus which has fewer moving parts than conventional storage units used for the same purpose.

A more specific object of the present invention is to provide a cryogenic storage apparatus wherein the formation of ice at an access opening to the apparatus is substantially reduced if not eliminated.

Related objects of the invention pertain to a method of storage.

These and other objects of the present invention will be apparent from the drawings and descriptions herein.

SUMMARY OF THE INVENTION

A storage unit comprises, in accordance with the present invention, housing defining a storage chamber, a carrier disposed inside the chamber for supporting a plurality of specimens in a predetermined array, and an access port on the housing for enabling access to the chamber for insertion and retrieval of specimens from the carrier. The access port includes an opening in the housing and a plug member removably located in the opening. The carrier is provided with a seat for receiving the plug member during an access operation, so that the plug member is located in the chamber during the access operation. A drive is operatively connected to the carrier for moving the carrier in the chamber to juxtapose different specimens to the access port. An insertion and removal mechanism is coupled to the housing for alternately inserting and removing specimens from the chamber via the access port during the access operation.

Where the storage unit is a cryogenic storage apparatus, the formation of ice at the access port is minimized. This reduction in ice is achieved largely because of the disposition of the plug or door member inside the cryogenic storage apparatus during insertion and retrieval operations. In prior machines, the door of the access port is retracted outwardly away from the machine, thus inducing the formation of ice crystals on the cold surfaces of the door member. The ice crystals must be removed prior to the refitting of the door to the access port. In a cryogenic storage apparatus in accordance with the present invention, the door or plug member is temporarily stored inside the apparatus, thereby preventing the formation of ice crystals during the access operation.

In accordance with a particular feature of the present invention, the plug or door member of the access port has a loose fit to the housing of the storage apparatus. For example, where the plug member is made of Styrofoam, the closure of the access port is not gas tight. Thus, cryogenic vapors (cooled $N_2$) can leak around the edges of the plug member. This leakage effectively serves as a safety valve, preventing an overpressurization of the cryogenic storage apparatus. Also, it is to be noted that the plug member is made of insulating material which inhibits the formation of ice along an outer surface.

It is contemplated that the plug member and the insertion and removal mechanism have cooperating elements for enabling the insertion and removal mechanism to move the plug member from the opening radially inwardly into the seat in the carrier prior to the access operation and for enabling the insertion and removal mechanism to move the plug member from the seat radially outwardly into the opening after the access operation. The cooperating elements may take the form of a suction device on the insertion and retrieval mechanism and a smooth surface, for example, in a recess in the plug member. Thus, although a separate mechanism may be provided for shifting the plug member alternately into and out of the seat in the carrier member, it is more efficient to have this operation performed by the same mechanism used to insert and remove vials or specimens.

Preferably, the carrier includes a drum and a cylinder connected thereto with the cylinder coaxially surrounding and being spaced from the drum. The drive is connected to the drum and the cylinder for rotating the drum and the cylinder about a vertical axis. The cylinder is provided with an array of horizontally and radially extending openings for receiving respective ones of the specimens.

The storage chamber is located between the drum and the inner surface of the housing. This layout reduces, if not minimizes, the volume of the storage chamber and thus increases cooling efficiency where the storage unit is a cryogenic storage apparatus. Also, the locations of the specimens are precisely defined and cannot shift, whether during normal usage or during extraordinary circumstances such as earthquakes.

Where the storage unit is a cryogenic storage apparatus, the housing is provided with a sump for holding a supply of a low-temperature liquid (e.g., liquid $N_2$). Also, the drum and the cylinder are made of a heat conductive material for facilitating a low-temperature storage of the specimens. It is preferred that the drum and the perforated cylinder are made of aluminum. Aluminum is a good thermal conductor and will reduce the thermal gradient from the top to the bottom of the storage chamber.

According to another feature of the present invention, the housing is provided with a retainer for cooperating with the plug member to hold the plug member in the opening. The retainer may comprise a magnet for exerting an attractive force on a magnetic or magnetizable element mounted to the plug member.

To facilitate storage of large numbers of specimens, the insertion and retrieval operations and the tracking of stored specimens are implemented by a computer. The computer is operatively connected to the insertion and retrieval mechanism.

A storage unit comprises, in accordance with the present invention, a housing with a sidewall defining a storage chamber, a carrier disposed inside the chamber for supporting a plurality of specimens in a predetermined cylindrical array, a drive operatively connected to the carrier for rotating the carrier about a vertical axis, an access port on the sidewall for enabling lateral access to the chamber for insertion and retrieval of specimens from the carrier, and an insertion and removal mechanism coupled to the housing for alternately inserting and removing specimens from the chamber via the access port.

The cylindrical array for the specimens is a particularly simple configuration. Access to an entire column of specimens is obtained through a longitudinal, vertical slot in the sidewall of the housing. The slot is preferably substantially coextensive with the carrier in a vertical direction. An elongate plug or door member is removably located in the slot. As discussed above, the plug member is temporarily stored in the storage chamber during access operations. To that end, the carrier is provided with a seat for receiving the plug member.

A method for storing a multitude of samples in accordance with the present invention utilizes a storage unit having a housing defining a storage chamber and further having a carrier disposed inside the chamber for supporting a plurality of specimens in a predetermined array. The method includes shifting a plug member inwardly into the storage chamber and away from an opening in the housing, moving the carrier to dispose a predetermined specimen receiving location on the carrier adjacent to the opening, inserting a specimen through the opening to the predetermined location on the carrier, and depositing the specimen at the predetermined location on the carrier. After the depositing of the specimen, the plug member is relocated back to the opening in the housing and thereafter shifting the plug member outwardly into the opening to thereby close the opening.

Preferably, the shifting of the plug member inwardly into the chamber and away from the opening includes shifting the plug member into a seat on the carrier and further includes moving the carrier to relocate the shifted plug member away from the opening. Also, the relocating of the plug member includes again moving the carrier to relocate the plug member back to the opening and to simultaneously transfer the deposited specimen away from the opening.

In accordance with a feature of the present invention, the shifting of the plug member includes operating an insertion and retrieval mechanism, while the inserting and depositing of the specimen includes operating the same insertion and retrieval mechanism. The insertion and retrieval mechanism preferably includes a suction device. An advantage of a suction device over mechanical or electromechanical servo-mechanisms is that the suction or vacuum feed line can be designed to retain the applied vacuum even in the event of a loss of power.

A storage unit with automatic insertion and retrieval in accordance with the present invention presents numerous and substantial benefits over existing technologies. The storage unit is more efficient, more reliable, and significantly less prone to accidents and failure. The storage unit has reduced insertion and retrieval times and a simpler construction than prior cryogenic storage devices. The storage unit has fewer moving parts than conventional cryogenic storage devices and accordingly has less need for maintenance. The formation of ice at the access opening to the apparatus is substantially reduced if not eliminated.

In a cryogenic storage unit in accordance with the present invention, liquid nitrogen use is decreased and temperature control is improved. Where electrical power or the liquid nitrogen supply is interrupted, temperature control remains in place for substantially longer periods than in prior cryogenic storage units.

DESCRIPTION OF THE PREFERRED EMBODIMENTS

Figure 1:
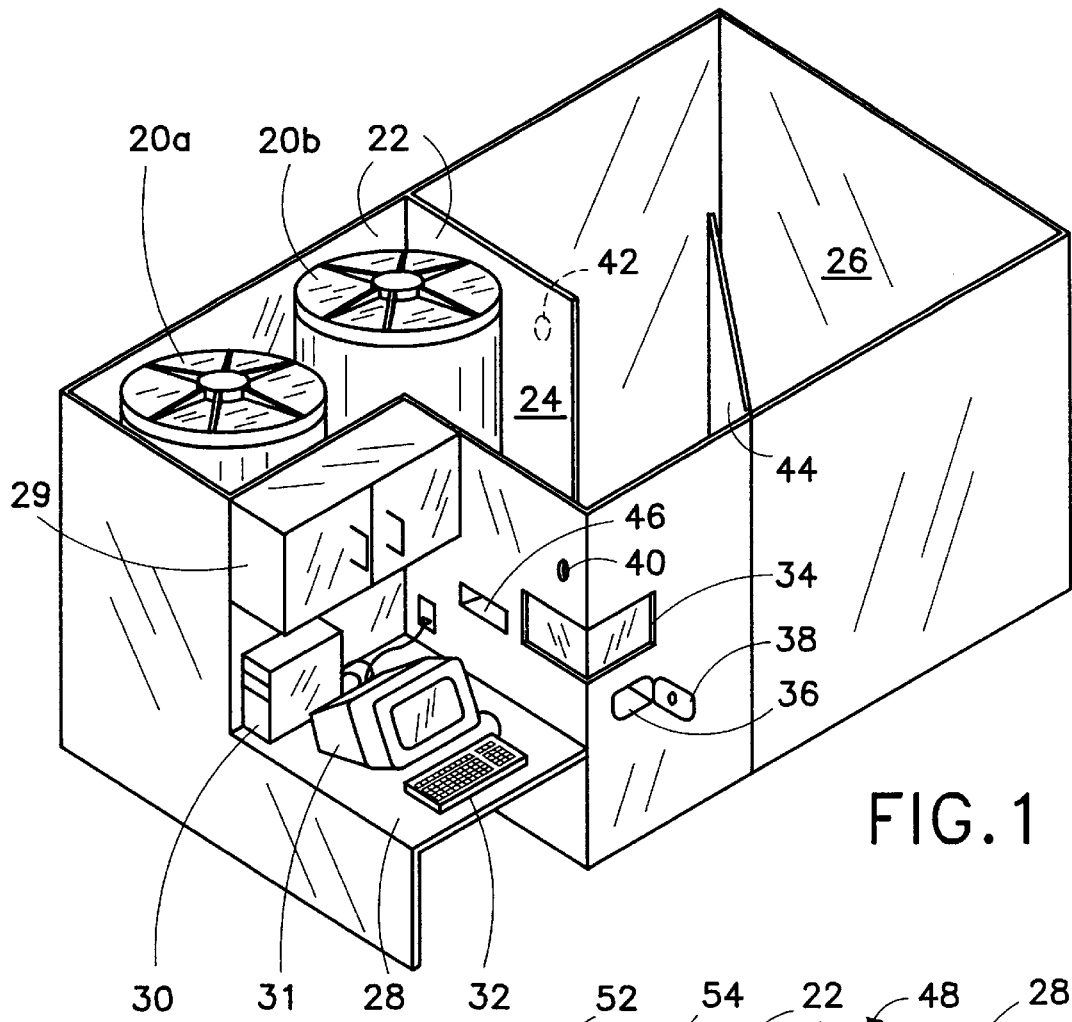
FIG. 1 is a schematic perspective view of a cryogenic storage installation with two cylindrical storage units in accordance with the present invention.

As illustrated in FIG. 1, a cryogenic storage installation includes a pair of cylindrical storage units 20a and 20b. Each unit 20a and 20b stores up to approximately 17,500 specimen-containing vials. Prefabricated walls 22 define a custom enclosure or space 24 containing storage units 20a and 20b. Walls 22 are modularly expandable to define one or more additional enclosures 26 for containing further cryogenic storage units (see FIGS. 2–5).

The storage installation includes an operator desk or station 28 with a utility cabinet 29 and a computer 30 including a monitor 31 and a keyboard 32. Computer 30 tracks the locations of specimens in storage units 20a and 20b and, by means of providing unique bar code identifications to a robot controller 30a (FIG. 11), controls access to storage units 20a and 20b in response to operator instructions. Walls 22 are provided with a window 34 enabling the operator to view the access operations from desk 28. Walls 22 are also provided with at least one opening 36 accessed via a door 38 for receiving a vial to be stored from the operator. During an automatic specimen storage or retrieval process, the operator monitors the process via window 34 and, if a malfunction is detected, will instruct computer 30 to abort the process. Alternatively, computer 30 may be bypassed by interrupting robot movements via a dedicated pushbutton 40. An additional abort control 42 (FIGS. 1 and 2) is provided outside a normally locked service door 44. Control 42 must be actuated to abort robot motion prior to an unlocking of door 44 to permit operator entry into enclosure 24.

As disclosed in U.S. Pat. Nos. 4,969,336 and 5,233,844, the disclosures of which are hereby incorporated by reference, the specimen-containing vials are provided with bar codes individually identifying the specimens or vials. A laser implemented bar code reader (not shown) is disposed inside enclosure 24 for reading the bar code and transmitting the encoded information to computer 30. In response to a preprogrammed storage sequence and/or in response to instructions from the operator, computer 30 controls the storage of the vial in a predetermined location in storage units 20a and 20b. When a specimen is to be extracted from storage units 20a or 20b, controller 30a (FIG. 11) accesses an internal data base on instructions from computer 30 to determine the location of the desired specimen in storage units 20a and 20b. The identity of a retrieved specimen or vial is verified by the bar code reader and computer 30 and the retrieved specimen or vial is deposited into a tray 46 for removal by the operator.

Figure 2:
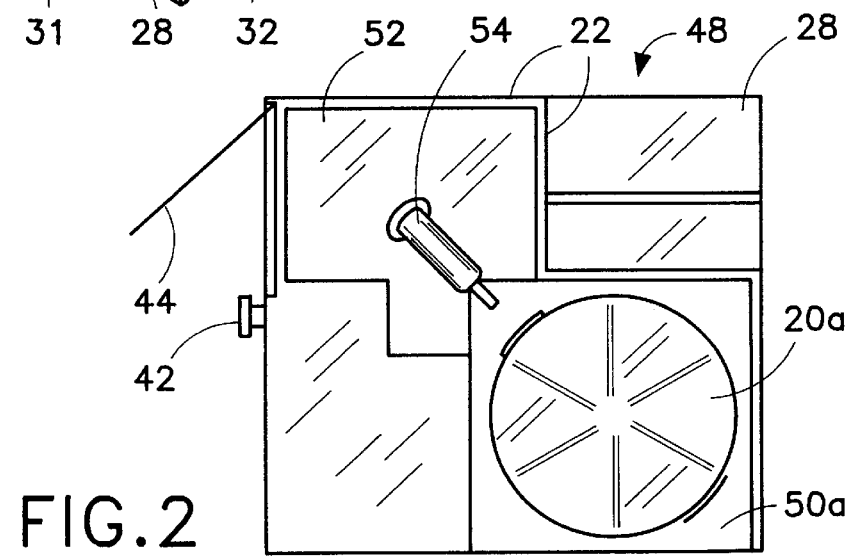
FIG. 2 is a schematic plan view of a cryogenic storage module including a single cylindrical storage unit in accordance with the invention.

As depicted in FIG. 2, a primary module 48 for a cryogenic storage facility includes a platform 50a on which cryogenic storage unit 20a is placed. Another platform 52 is disposed contiguously to platform 50a for supporting a robotic insertion and retrieval arm or mechanism 54.

Figure 3:
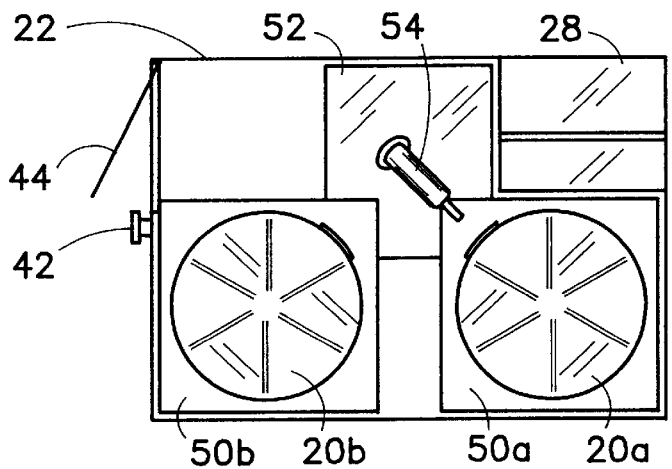
FIG. 3 is a plan view of the cryogenic storage module of FIG. 2, including an additional cylindrical storage unit in accordance with the invention.

FIG. 3 shows the primary module 48 of FIG. 2 with cryogenic storage unit 20b disposed on a respective platform 50b which is positioned adjacent to platform 52 to enable accessing of storage unit 20b by robotic insertion and retrieval mechanism 54.

Figure 4:
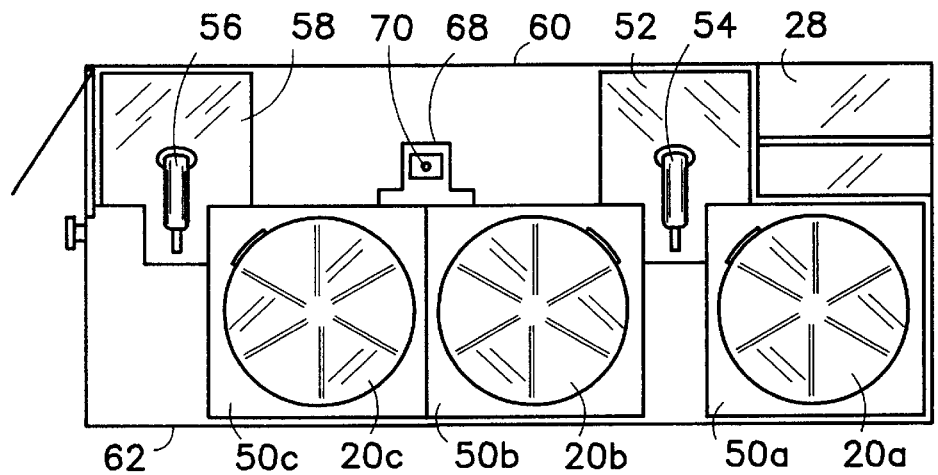
FIG. 4 is a schematic plan view of two cryogenic storage modules according to FIG. 3, including a total of three cylindrical storage units in accordance with the invention.

In FIG. 4, the cryogenic storage facility of FIG. 3 has been expanded to incorporate another robotic insertion and retrieval mechanism 56 and an additional cryogenic storage unit 20c supported on respective mutually contiguous platforms 58 and 50c. The enclosure walls 22 of the storage facility of FIGS. 2 and 3 have been extended to have longer side walls 60 and 62.

Figure 5:
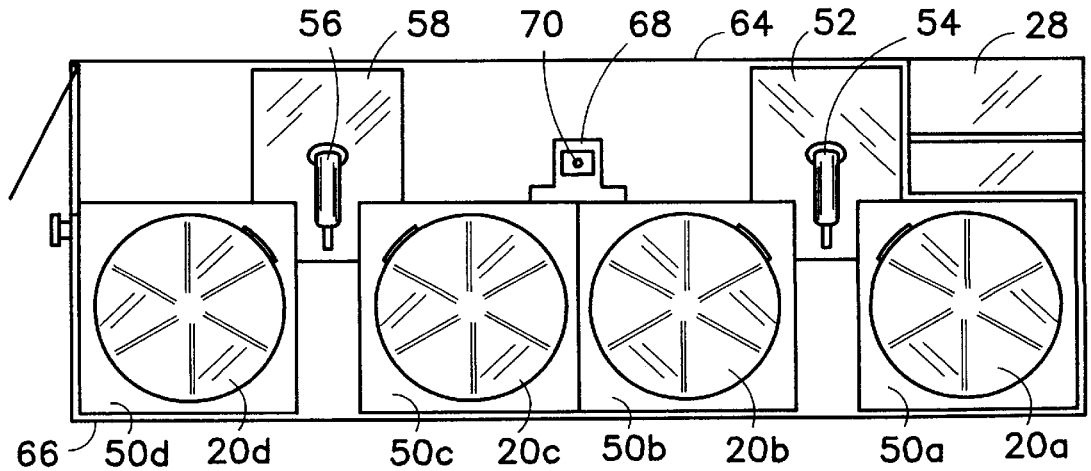
FIG. 5 is a schematic plan view of the two cryogenic storage modules of FIG. 4, with an additional cylindrical storage unit in accordance with the invention.

A further storage facility expansion is shown in FIG. 5. Another platform 50d with a respective additional storage unit 20d has been placed in contiguity with platform 58 for enabling automatic access to storage unit 20d by insertion and retrieval mechanism 56. Also, longer side walls 64 and 66 are provided. Each robotic insertion and retrieval mechanism 54 and 56 serves a maximum of two storage units 20a and 20b or 20c and 20d. Personal computer 30 serves a maximum or two robotic insertion and retrieval mechanisms 54 and 56 and four storage units 20a, 20b, 20c, and 20d.

Access to storage units 20a, 20b, 20c, and 20d by insertion and retrieval mechanisms 54 and 56 is effectuated under the control of a single computer 30 (FIG. 1) at operator desk, station 28. To that end, insertion and retrieval mechanisms 54 and 56 cooperate with one another to transfer specimen-containing vials from one insertion and retrieval mechanisms 54 or 56 to the other in the event that storage unit 20c or 20d is used for storage. A transfer platform 68 may be provided for establishing a transfer location. Transfer platform my be provided with a holder 70 for temporarily keeping a vial.

Storage units 20a–20d are individually realizable as a cryogenic storage unit 20 illustrated in FIGS. 6–9. Storage unit 20 is disposed on an aluminum two-inch platform 71 (e.g., platforms 50a–50d) provided with ground or floor supports 73 which are adjustable for leveling purposes. Platform 71 is provided with bores 75 for receiving connector pins or dowel bolts (not shown) for fixing the platform to an adjacent platform 156 (FIG. 10). Storage unit 20 includes an insulated dewar-type outer housing or vessel 72 provided in a cylindrical sidewall 74 with an elongate access slot or opening 76 (FIGS. 6, 8, 9, 10) defined or framed by elongate lateral flanges 78 and 80 and arcuate upper and lower flanges or retention plates 82 and 84 all of which extend outwardly from sidewall 74.

Figure 6:
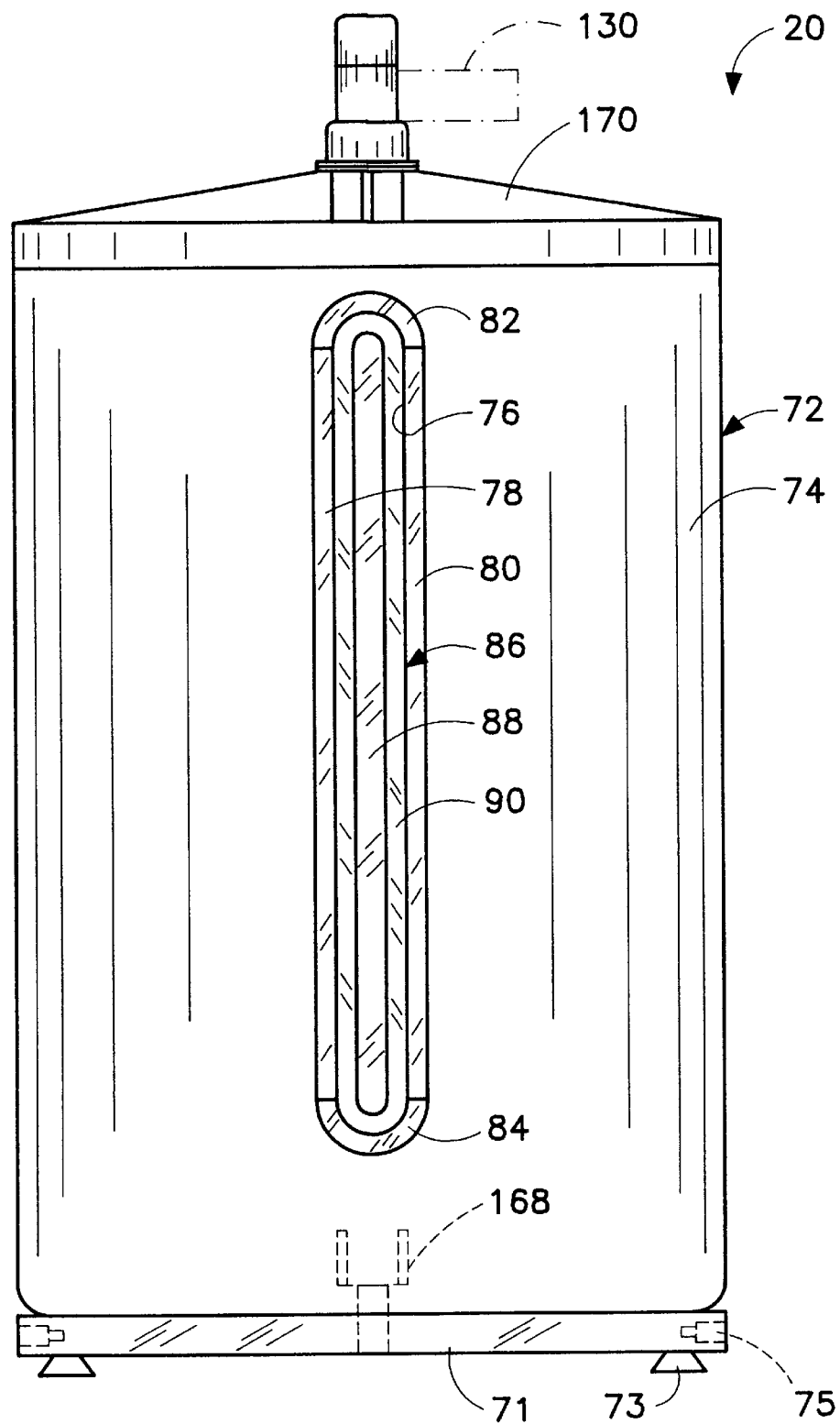
FIG. 6 is a side elevational view of a cryogenic storage unit in accordance with the present invention.

Access opening 76 is closed by an elongate plug member or sealing wedge 86. Plug member 86 is made of an insulating material such as Styrofoam. As illustrated in FIG. 6, plug member 86 may comprise an inner wedge element 88 and an outer wedge element 90 which surrounds the inner element 88. This bipartite configuration of plug member 86 enables a variation in the size of specimen-containing vials stored in unit 20. Where all vials stored in vessel 72 are up to one inch in diameter, outer wedge element 90 remains in place lining access opening 76, thereby reducing the width of the access opening. When the stored inventory includes vials with a diameter between one and two inches, outer wedge element 90 is locked to inner wedge element 88 and moves therewith during access operations.

Figure 7:
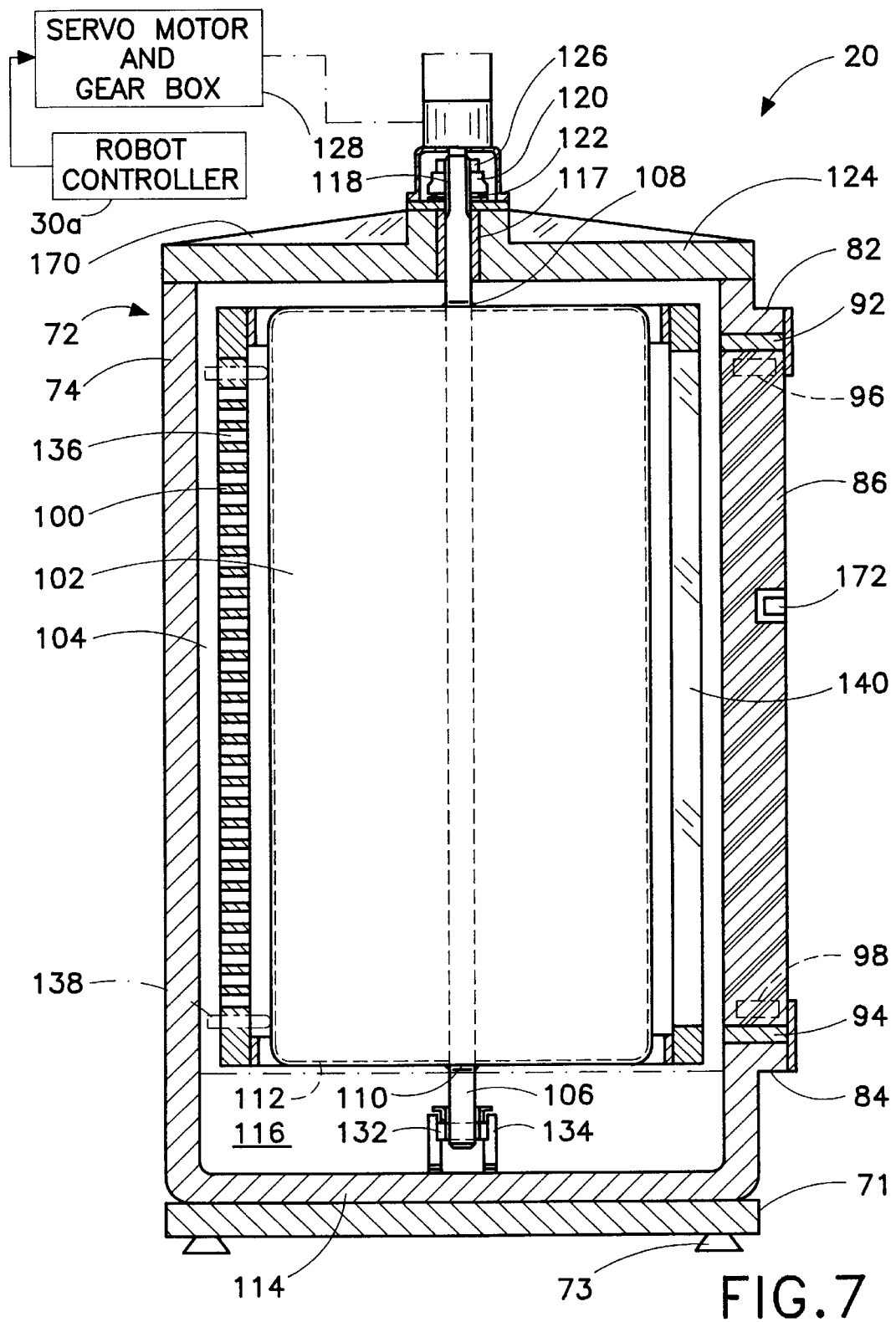
FIG. 7 is a vertical cross-sectional view of the cryogenic storage unit of FIG. 6, showing a plug member (86) wedged into an elongate vertical access opening.
Figure 8:
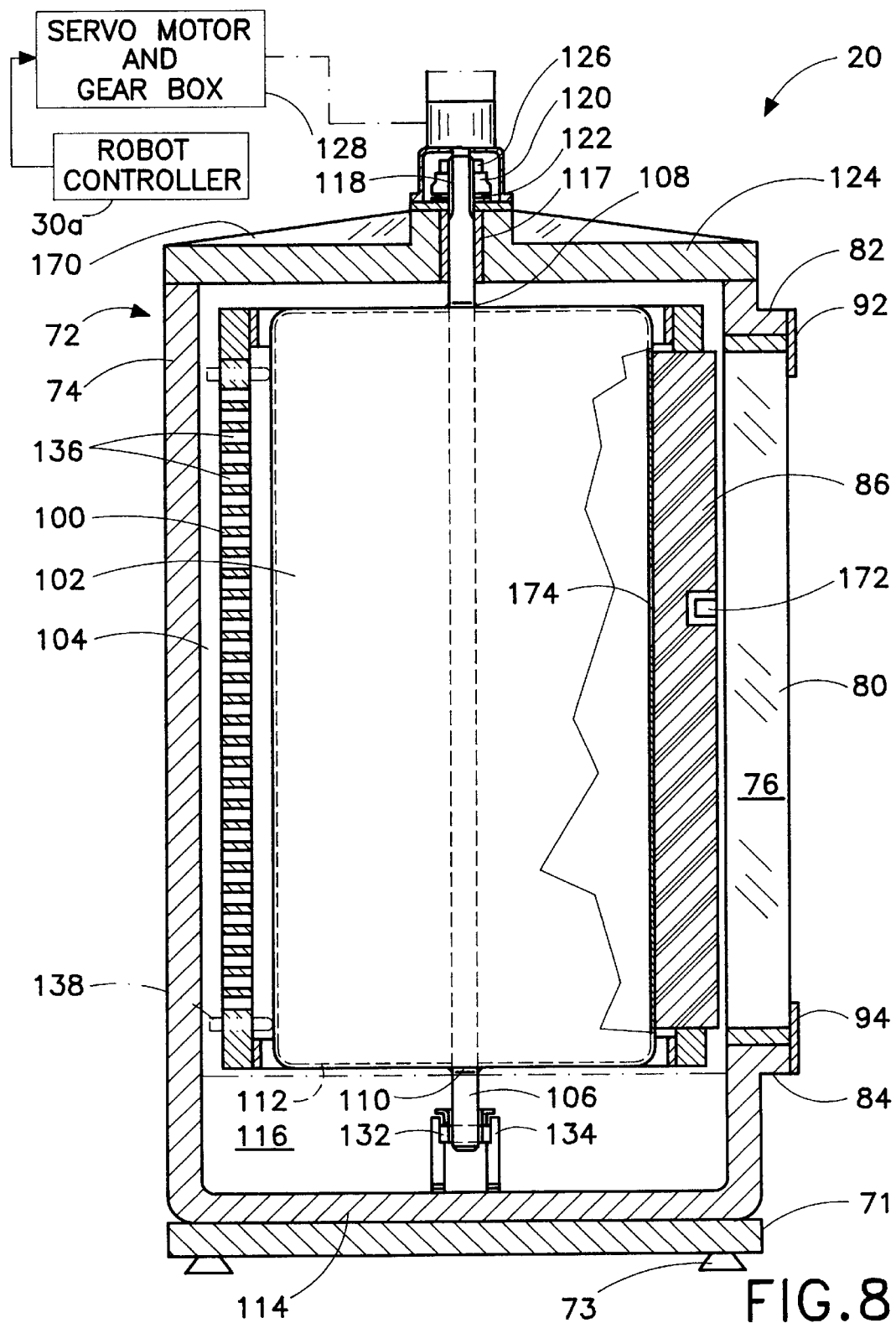
FIG. 8 is a cross-sectional view similar to FIG. 7, showing the plug member (86) inserted into a slot provided in a cylindrical specimen carrier in the storage unit.

Alternatively, rather than having a bipartite construction, plug member 86 may be a unitary piece, as depicted in FIGS. 7 and 8. At upper and lower ends, along inner surfaces of upper and lower flanges 78 and 80, access opening 76 (FIG. 6) is provided with magnetic retainers 92 and 94 (FIG. 7, etc.) which cofunction with magnetic elements 96 and 98 in plug member 86 to retain the plug member in access opening 76.

Figure 9:
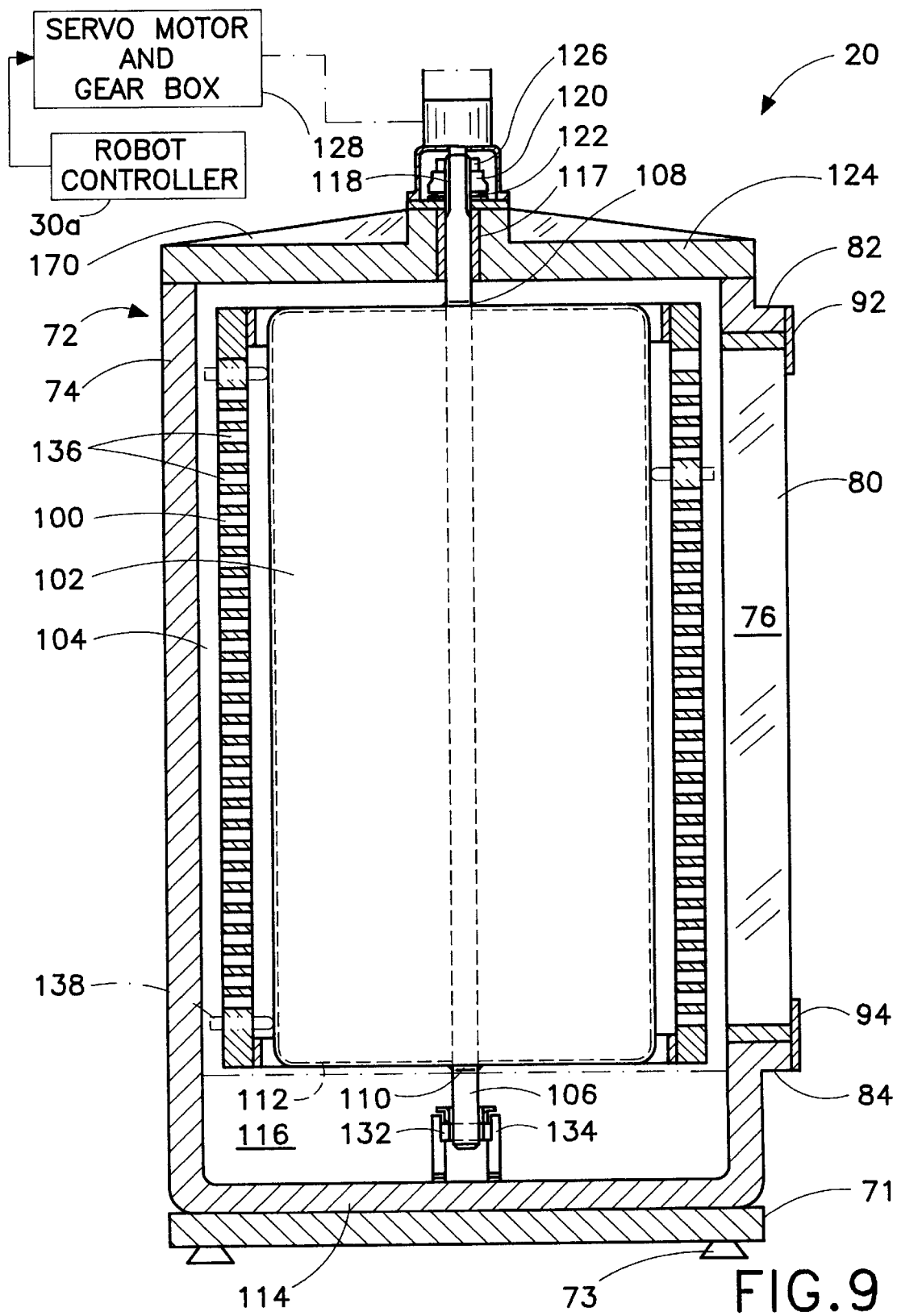
FIG. 9 is a cross-sectional view similar to FIGS. 7 and 8, showing the cylindrical specimen carrier rotated to a position to dispose specimen-containing vials adjacent to the access opening.
Figure 10:
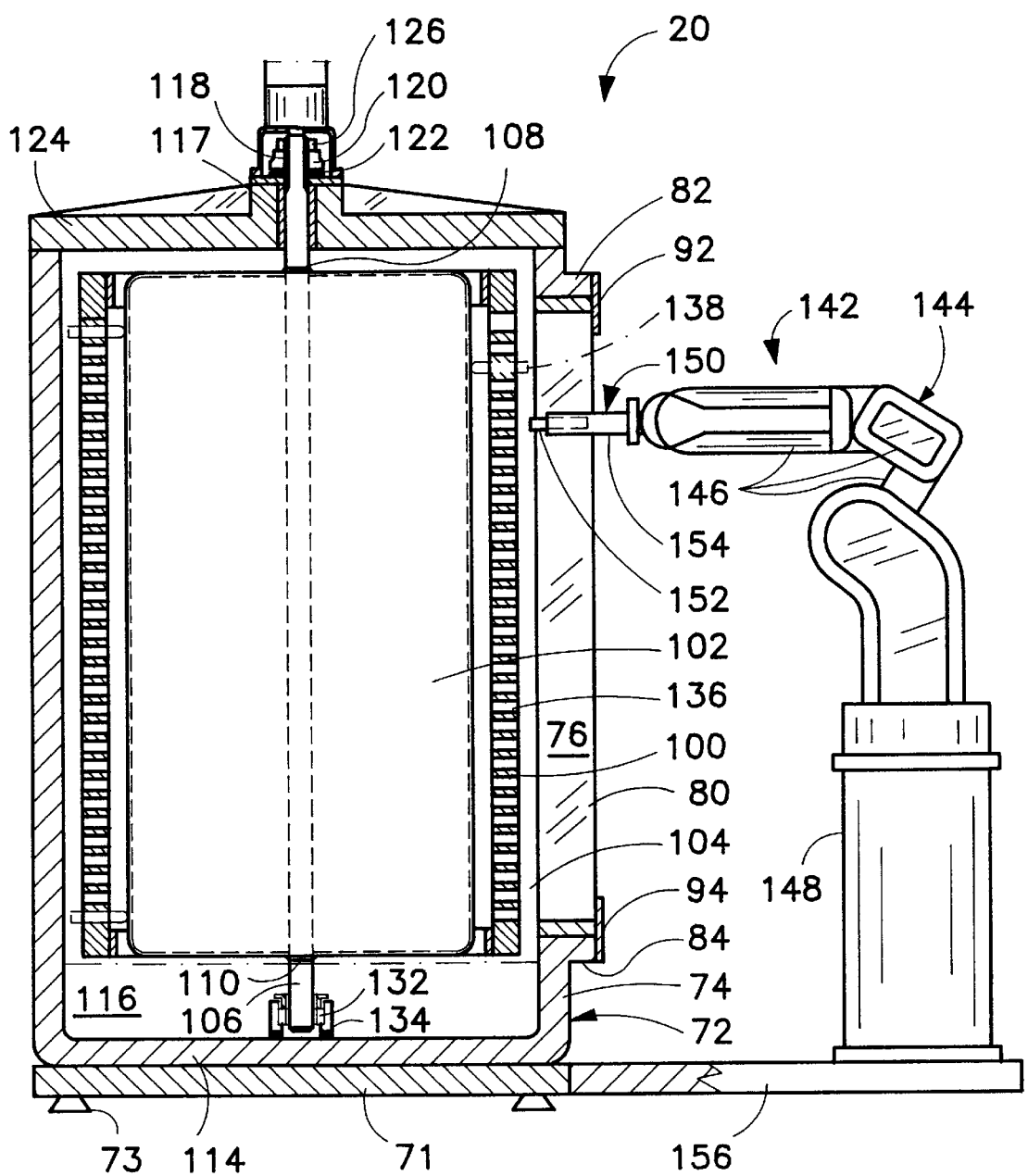
FIG. 10 is a cross-sectional view of the storage unit similar to FIG. 9, additionally showing in elevational view a robotic insertion and retrieval mechanism.

As illustrated in FIGS. 7–9, vessel 72 contains a cylindrical aluminum specimen carrier 100 rigidly mounted to and spaced from a thin-walled aluminum drum 102. Drum 102 is evacuated to a high vacuum and sealed and, together with sidewall 74, defines a cylindrical storage space or chamber 104. Drum 102 is fixed to an aluminum drive shaft 106 which extends vertically through the drum and is welded thereto at 108 and 110, thereby sealing the drum. A lower panel 112 of drum 102 is spaced from a base 114 of vessel 72 to define a sump 116 containing a supply of a cryogenic fluid such as liquid nitrogen ($N_2$).

At an upper end, drive shaft 106 is rotatably journaled in a sleeve bearing 117 made of polytetrafluoroethylene and is provided with an externally threaded portion 118. A nut 120 is threaded to shaft portion 118 and cooperates with a medium-duty thrust roller bearing 122 in suspending drive shaft 106, as well as drum 102 and specimen carrier 100, from an upper panel 124 of vessel 72. The relative vertical locations of drive shaft 106 and nut 120 are adjustable during an installation procedure to set the vertical position of specimen carrier 100 relative to vessel 72 and particularly with respect to access opening 76. Nut 120 is locked to drive shaft 106 by a jam nut 126.

Drive shaft 106 is rotated by an extremely low lost motion (backlash) servomotor and gear box 128. Preferably, a right angled configuration of the servomotor and gear box is employed, as indicated in phantom lines 130 in FIG. 6. The servomotor is energized under the control of robot controller 30a as instructed by computer 30.

At a lower end, drive shaft 106 is trapped and guided by a spherical bearing 132 made of polytetrafluoroethylene and disposed in a housing 134 welded to base 114 of vessel 72.

Figure 13:
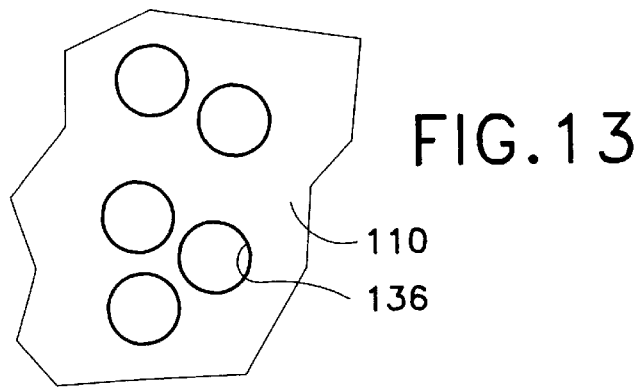
FIG. 13 is a partial side-elevational view of the specimen carrier of FIGS. 8 and 9.

Specimen carrier 100 is formed with a multitude of perforations or holes 136 in a close packed accurately machined array, as illustrated in FIG. 13. In FIGS. 7–10, perforations 136 are only shown in the sectioned portions of carrier 100, for purposes of simplifying the drawing. Perforations 136 are intended to receive and hold respective specimen-containing vials 138 so that the vials are oriented horizontally and radially relative to carrier 100, drum 102 and drive shaft 106. The radial positions of vials 138 are restricted along an inner side by drum 102 and along an outer side by an inner surface (not separately designated) of vessel sidewall 74. During a deposition operation, vials 138 are inserted into respective perforations 136 so that the radially inner ends of the vials are placed in contact with drum 102. Because drum 102 and carrier 100 are made of aluminum, which is an efficient thermal conductor, the specimens are easily maintained at cryogenic temperatures and the thermal gradient from the top to the bottom of storage chamber 104 is minimized. Because storage chamber 104 has a small volume (less than ⅓ that of a comparably sized machine having a structure disclosed in U.S. Pat. No. 5,233,844), the utilization of liquid nitrogen is reduced. In addition, evaporation of the liquid nitrogen is reduced because of improved dewar sealing techniques.

As illustrated in FIG. 7, carrier 100 is provided with an elongate vertical slot 140 which together with the outer surface of drum 102 defines a seat for receiving plug member 86 during an access operation. Prior to an access operation, when storage unit 20 is in a quiescent state, plug member 86 is disposed or wedged in access opening 76, as shown in FIG. 8, thereby closing vessel 72. Slot 140 is always disposed adjacent to access opening 76, except when drum 102 and carrier 100 are rotated to bring a selected column of vials 138 into juxtaposition with access opening 76. At the beginning of the access operation, plug member 86 is pushed radially inwardly from access opening 76 into slot 140 so as to be seated against drum 102 and in slot 140, as illustrated in FIG. 8. Servomotor and gear box 128 is then activated by controller 30a and computer 30 to rotate shaft 106 and concomitantly drum 102 and carrier 100, thereby aligning a column of vials 138 with the opened access opening 76, as depicted in FIG. 9.

FIG. 10 shows the cryogenic storage unit 20 in the access ready state of FIG. 9 together with a robotic insertion and retrieval mechanism 142 which is an embodiment of insertion and retrieval mechanisms 54 and 56 (FIG. 5). Mechanism 142 includes an arm 144 having a plurality of articulated arm parts 146 connected at one end to a pedestal 148 and provided at an opposite with a suction device 150. Suction device 150 comprises a vial suction cup or vacuum applicator 152 disposed inside a cylinder 154. Pedestal 148 is anchored to platform 156. Platform 156 is a two-inch-thick aluminum plate.

Platforms 71 and 156 are dowel bolted together in the factory for calibration purposes and then disassembled for shipment. In the field, platforms 71 and 156 are dowel bolted back together with minimal, if any, recalibration requirement. It is to be noted that platform 156 may be pre-reamed in preparation for attachment to another dewar platform 71 in the field.

Figure 11:
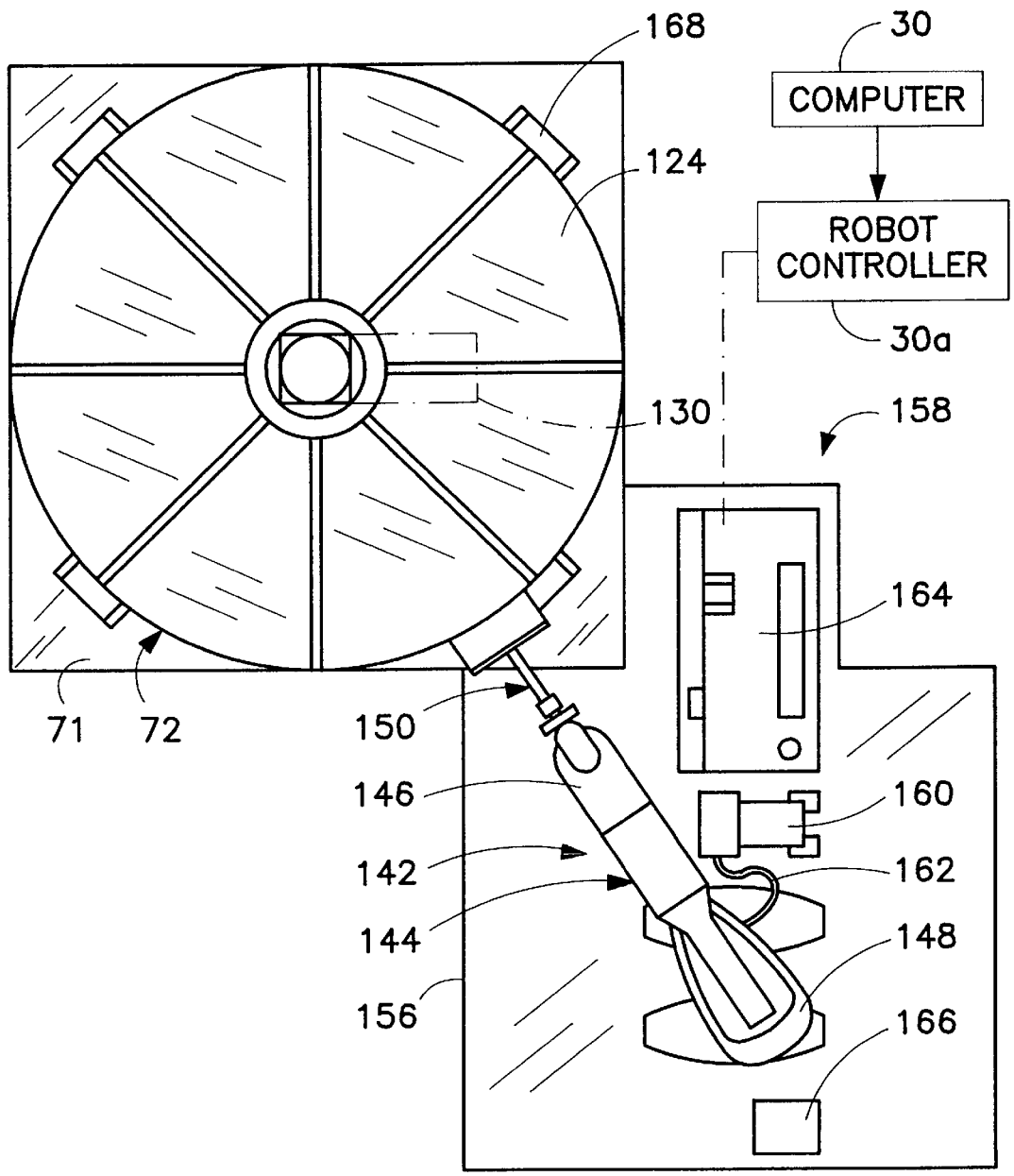
FIG. 11 is a top plan view of the storage unit and robotic insertion and retrieval mechanism of FIG. 10.

As depicted in FIG. 11, insertion and retrieval mechanism 142 is part of an insertion and retrieval apparatus 158 which further includes a vacuum pump 160. Pump 160 is fixed to platform 156 and connected via a vacuum hose 162 to mechanism 142. A controller 164 is operatively connected to computer 30 and to mechanism 142 for controlling mechanism 142 in response to signals from computer 30. An adjustment device 166 is provided for removing, from an overhang of platform 156, sag arising from incipient vibration.

FIG. 11 further depicts mounts 168 needed for accommodate the seating of vessel 72 on platform 71 (see also FIG. 6). The upper panel 124 of vessel 72 is provided along an upper side with triangular reinforcement brackets 170.

In order to shift or relocate plug member 86 from access opening 76 to slot 140 on specimen carrier 100, plug member 86 is provided with a lined recess 172 (FIGS. 7–10) into which suction cup or vacuum applicator 152 is inserted. For holding plug member 86 in its seat in slot 140 during a rotation of drum 102, the drum is provided with a magnetic retainer 174 (FIG. 8) which coacts with a magnetic element (not illustrated) disposed in or on plug member 86.

Figure 12:
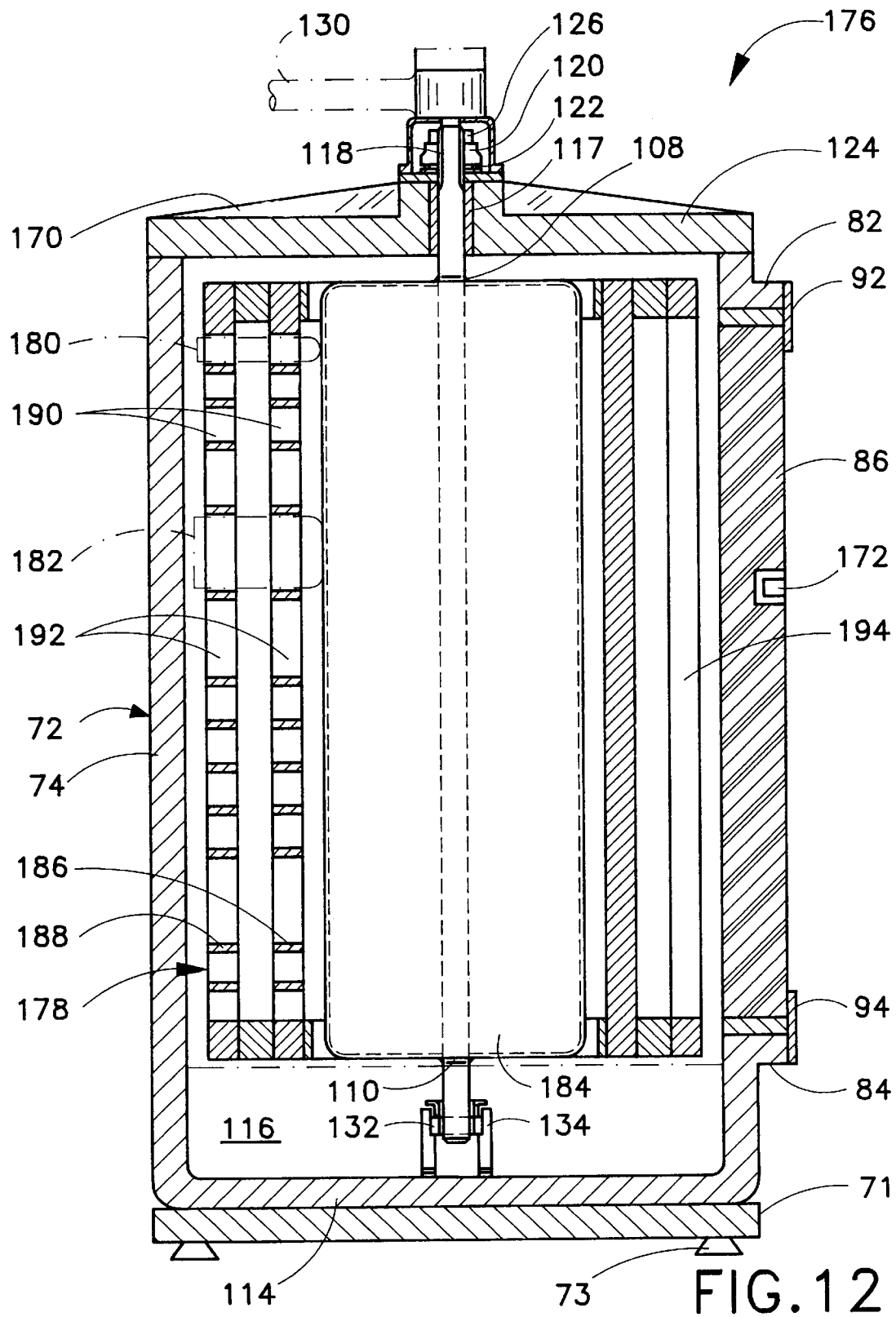
FIG. 12 is a longitudinal or vertical cross-sectional view of another embodiment of a cryogenic storage apparatus in accordance with the present invention, showing differently sized biological containers in storage.

FIG. 12 illustrates a modified cryogenic storage unit 176 wherein structures identical to structures in storage unit 20 of FIGS. 6–10 have been designated with the same reference numerals. Storage unit 176 includes a specimen carrier 178 which has been modified to support specimen-containing vials 180 and 182 of different diameters. In addition, storage unit 176 includes a drum 184 which has a smaller diameter than drum 102 (FIGS. 7–10), thereby accommodating vials 180 and 182 which are longer than vials 138.

Carrier 178 is fixed to drum 184 and includes an aluminum inner cylinder 186 and an aluminum outer cylinder 188 which are spaced from one another, as well as from the inner surface of vessel sidewall 74 and drum 184. Cylinders 186 and 188 are provided with myriad holes 190 and 192 which are differently sized for purposes of receiving vials 180 and 182, respectively. As discussed above with reference to the placement of vials 138 in carrier 100, the radially inner ends of vials 180 and 182 are in contact with drum 184. Outer cylinder 188 is provided with a longitudinally extending slot 194 for receiving plug member 86 during an access operation. The bipartite construction of plug member 86 discussed above with reference to FIG. 6 is particularly useful in the embodiment of FIG. 12. Only inner wedge element 88 need be relocated into slot 194 if the vial being moved into or out of storage is a narrow vial 180. Where the vial being moved is a wide vial 182, both wedge elements 88 and 90 must be shifted from the access opening 76 to enable passage of the wide vial through the access opening. Generally, where both narrow vials 180 and wide vials 182 are stored, wedge elements 88 and 90 are shifted as a single unit, regardless of whether a narrow vial 180 or a wide vial 182 is being moved into or out of storage.

Figure 14:
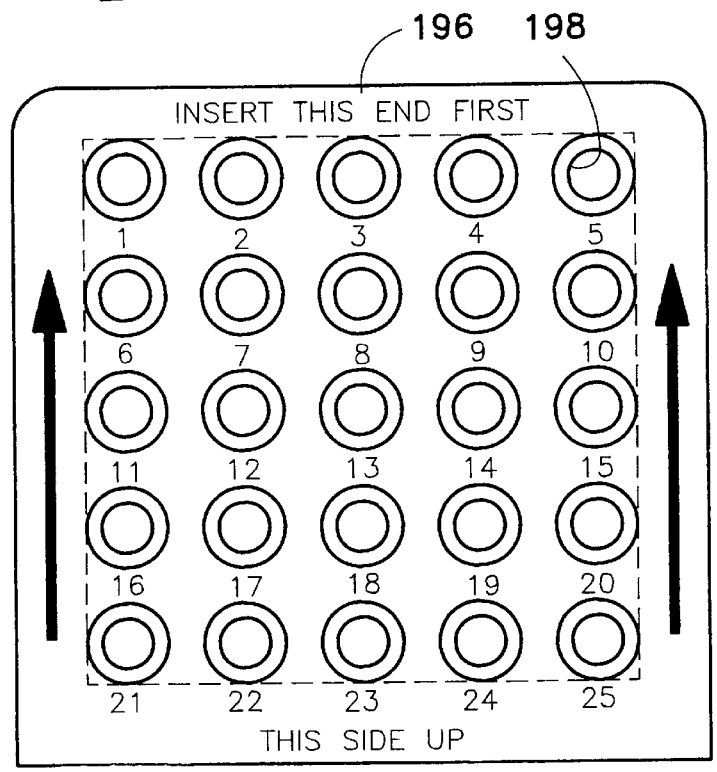
FIG. 14 is a top plan view of a tray for multiple specimen-containing vials.
Figure 15:
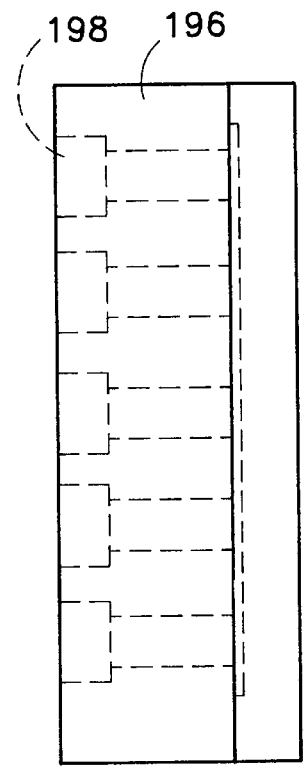
FIG. 15 is a side elevational view of the tray of FIG. 14.
Figure 16:
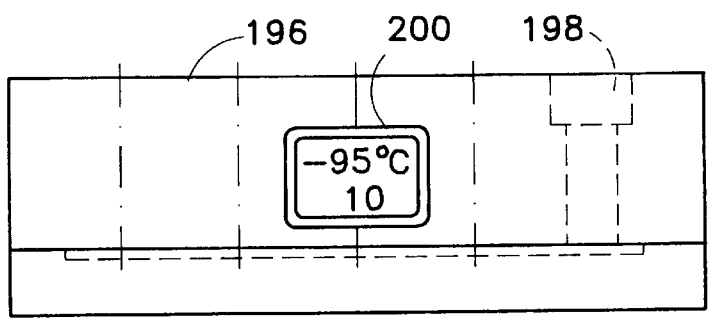
FIG. 16 is an end elevational view of the tray of FIG. 14.

In the cryogenic storage of such specimens as blood cells, the specimen temperature is lowered in a controlled fashion to −95° C. prior to the placement of the specimen into long term storage at −196° C. This reduction in specimen temperature is accomplished by employing a device known as a Control Rate Freezer. Such a device is known from U.S. Pat. No. 5,176,202. Typically, a Control Rate Freezer processes up to 25 vials or specimens simultaneously. FIGS. 14–16 depict a thermally insulated temporary storage device or holder body 196 which can be used in both a Control Rate Freezer and at long term storage sites. Storage device 196 is provided with 25 recesses 198 which have profiles conforming to received vials 138 or 180 or 182 (not shown in FIGS. 14–16). Up to 25 vials 138 are temporarily stored in device 196 until insertion and retrieval mechanism 142 removes the vials for long term storage in unit 20. Device 196 serves to maintain vials 138 at the lowered temperature of approximately −95° C. for a period long enough to accommodate the complete long term storage cycle.

Device 196 represents an advance over current devices because device 196 is thermally insulated and enables bar code verification. Device 196 includes a display 200 indicating the low temperature of the vials. Display 200 may be connected to a temperature sensor (not shown) mounted to the device 196 for providing a continuously updated temperature read-out.

Robot teaching to account for dimensional differences in storage units 20 in the field will be accomplished by robot software and sensor sighting of the bottom hole or slot sensing. Vial locations can be checked periodically by software, as required.

In a cryogenic storage apparatus as described hereinabove, vial inventory space is minimized. Also, the thermal gradient from the top to the bottom of the vial storage space is kept to a minimum. Vials are sandwiched or trapped between drum 102 and the inner surface of vessel 72 so that there is no possibility of a vial address change following an earthquake or other catastrophe. Variation in temperature at the access opening is reduced over existing designs. In particular, since plug member 86 never leaves vessel 72 during a vial storage or retrieval operation, the temperature of the plug member in the vicinity of the vials is always at cryogenic temperatures. Moreover, other than a single adjustment in the vertical position of drum 102 relative to vessel 72, no fitting, spacing, adjustment or robot teaching is required. A cryogenic storage unit 20 as described herein has an increased liquid nitrogen capacity compared to existing automated cryogenic storage units and is capable of low temperature storage for extended periods even in the absence of electrical power or replenishment of cryogenic fluid.

Figure 17:
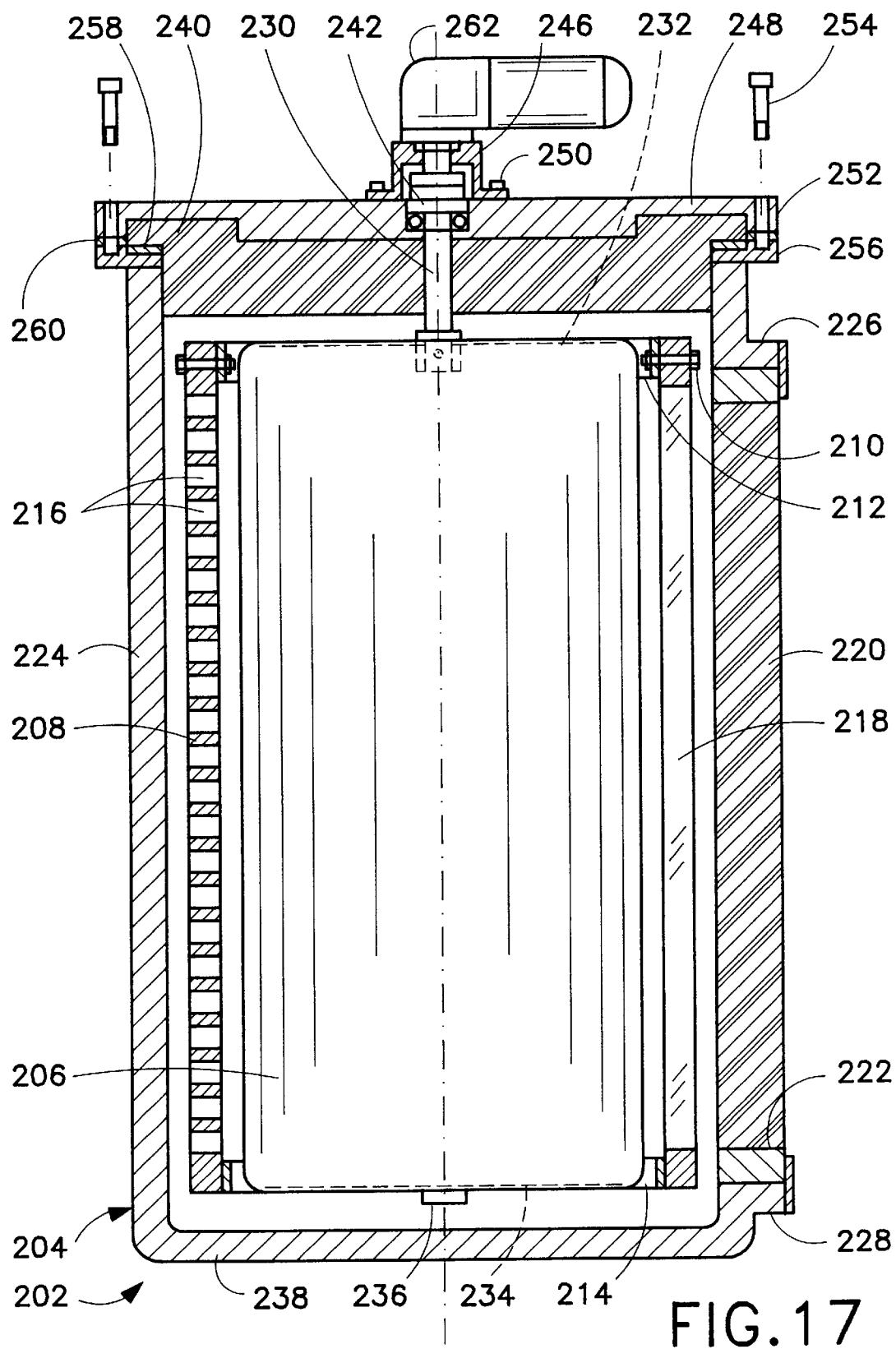
FIG. 17 is a vertical cross-sectional view of a modified cryogenic storage unit in accordance with the present invention.

FIG. 17 illustrates a cryogenic storage unit 202 including an insulated dewar-type outer housing or vessel 204, a hollow aluminum drum 206, and a cylindrical specimen carrier 208. Carrier 208 is connected to drum 206 via welding and/or bolts 210 and brackets 212, 214 and is provided with a dense array of vial-receiving perforations 216. Carrier 208 is further provided with an elongate slot 218 for seating a plug member 220 during an access operation., as described above. Plug member 220 is normally received in an elongate access opening 222 provided in a cylindrical sidewall 224 of storage vessel 204. Opening 222 is defined or framed by elongate lateral flanges (not shown) and arcuate upper and lower flanges or retention plates 226 and 228 which extend outwardly from sidewall 224.

Drum 206 is fixed to an aluminum drive shaft 230 which extends vertically through the drum and is welded thereto at upper and lower panels 232 and 234 of the drum, thereby sealing drum 206. A lower end 236 of shaft 230 is spaced from a base 238 of vessel 204. A pool (not shown) of liquid nitrogen is disposed at the bottom of vessel 204.

Shaft 230 and accordingly drum 206 and carrier 208 are supported only at an upper end of the shaft. At its upper end, drive shaft 230 extends through a 5-inch-thick slab of thermal polymeric material 240 and is rotatably journaled in an angular contact bearing 242. Contact bearing 242 is disposed in a housing 246 and is supported on a 2-inch-thick aluminum cover plate 248. Housing 246 is attached to cover plate 248 via bolts 250.

Cover plate 248 is coupled along its periphery 252 to vessel 204 via a plurality of bolts 254 and an annular flange 256 which is welded to an upper rim (not designated) of the dewar-type vessel 204. A silicone rubber gasket 258 is seated in a recess (not labeled) of flange 256 and is sandwiched between flange 256 and polymeric slab 240. The pressure placed on gasket 258 is controlled by the disposition of spacers 260 between flange 256 and the periphery 252 of cover plate 248.

Shaft 230 is held not only by angular contact bearing 242 but also by a gear motor 262. These two bearing points are sufficient to position drum 206 and carrier 208 inside vessel 204 with acceptable precision. The spherical bearing 132 (FIGS. 7–9) at the lower end of drive shaft 106 has been eliminated. This design not only eliminates positioning and assembly problems but also eliminates a source of failure: a bearing disposed for long periods in an extremely low-temperature environment is prone to malfunction.

The functioning and operation of cryogenic storage unit 202 are the same as the functioning and operation of cryogenic storage unit 20.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof

What is claimed is:

1. A storage unit comprising:
   a housing defining a storage chamber, said housing having a sidewall;
   a carrier disposed inside said chamber for supporting a plurality of specimens in a predetermined cylindrical array;
   a drive operatively connected to said carrier for rotating said carrier about a vertical axis;
   an access port on said sidewall for enabling lateral access to said chamber for insertion and retrieval of specimens from said carrier, said access port including an elongate vertically extending slot in said sidewall and further including an elongate plug member removably located in said slot, said slot being substantially coextensive with said carrier in a vertical direction; and
   an insertion and removal mechanism coupled to said housing for alternately inserting and removing specimens from said chamber via said access port.

2. The storage unit defined in claim 1 wherein said carrier is provided with a seat for receiving said plug member during an access operation, so that said plug member is located in said chamber during said access operation.

3. The storage unit defined in claim 2 wherein said plug member and said insertion and removal mechanism have cooperating elements for enabling said insertion and removal mechanism to move said plug member from said slot radially inwardly into said seat prior to an access operation and for enabling said insertion and removal mechanism to move said plug member from said seat radially outwardly into said slot after said access operation.

4. The storage unit defined in claim 3 wherein said carrier includes a drum and a cylinder coaxially surrounding and spaced from said drum, said cylinder being provided with an array of horizontally and radially extending openings for receiving respective ones of said specimens.

5. The storage unit defined in claim 4 wherein said housing is provided with a sump for holding a supply of a low-temperature liquid, said drum and said cylinder being made of a heat conductive material for facilitating a low-temperature storage of said specimens.

6. The storage unit defined in claim 5 wherein said slot is substantially coextensive with said carrier in a vertical direction.

7. The storage unit defined in claim 3 wherein said cooperating elements include a suction applicator on said insertion and removal mechanism.

8. The storage unit defined in claim 1 wherein said sidewall is provided with a retainer for cooperating with said plug member to hold said plug member in said slot.

9. The storage unit defined in claim 8 wherein said retainer is magnetic, said plug member being provided with magnetic elements.

10. The storage unit defined in claim 1 wherein said housing is provided with a sump for holding a supply of a low-temperature liquid, said plug member having a fit in said slot enabling pressure release.

11. The storage unit defined in claim 1 wherein said carrier includes a drum and a cylinder coaxially surrounding and spaced from said drum, said cylinder being provided with an array of horizontally and radially extending openings for receiving respective ones of said specimens.

12. The storage unit defined in claim 11 wherein said housing is provided with a sump for holding a supply of a low-temperature liquid, said drum and said cylinder being made of a heat conductive material for facilitating a low-temperature storage of said specimens.

13. The storage unit defined in claim 1 wherein said insertion and retrieval mechanism includes a suction applicator.

14. The storage unit defined in claim 1 wherein said chamber is cylindrical and said specimens are disposed in said chamber radially relative to said axis.

15. The storage unit defined in claim 1, further comprising a computer operatively connected to said insertion and removal mechanism for automatically tracking the locations of specimens in said housing and for controlling the insertion and removal of specimens from said chamber.

16. A storage unit comprising:
   a housing defining a storage chamber;
   a carrier movably disposed inside said chamber for supporting a plurality of specimens in a predetermined array;
   an access port on said housing for enabling access to said chamber for insertion and retrieval of specimens from said carrier, said access port including an opening in said housing and a plug member removably located in said opening, said carrier being provided with a seat for receiving said plug member during an access operation, so that said plug member is located in said chamber during said access operation;
   a drive operatively connected to said carrier for moving said carrier in said chamber to juxtapose different specimens to said access port; and
   an insertion and removal mechanism coupled to said housing for alternately inserting and removing specimens from said chamber via said access port during said access operation.

17. The storage unit defined in claim 16 wherein said plug member and said insertion and removal mechanism have cooperating elements for enabling said insertion and removal mechanism to move said plug member from said opening radially inwardly into said seat prior to said access operation and for enabling said insertion and removal mechanism to move said plug member from said seat radially outwardly into said opening after said access operation.

18. The storage unit defined in claim 17 wherein said carrier includes a drum and a cylinder coaxially surrounding and spaced from said drum, said drive being connected to said drum and said cylinder for rotating said drum and said cylinder about a vertical axis, said cylinder being provided with an array of horizontally and radially extending openings for receiving respective ones of said specimens.

19. The storage unit defined in claim 18 wherein said housing is provided with a sump for holding a supply of a low-temperature liquid, said drum and said cylinder being made of a heat conductive material for facilitating a low-temperature storage of said specimens.

20. The storage unit defined in claim 17 wherein said cooperating elements include a suction applicator on said insertion and removal mechanism.

21. The storage unit defined in claim 16 wherein said housing is provided with a retainer for cooperating with said plug member to hold said plug member in said opening.

22. The storage unit defined in claim 16 wherein said housing is provided with a sump for holding a supply of a low-temperature liquid, said plug member having a fit in said slot enabling pressure release.

23. The storage unit defined in claim 16 wherein said carrier includes a drum and a cylinder coaxially surrounding and spaced from said drum, said cylinder being provided with an array of horizontally and radially extending openings for receiving respective ones of said specimens.

24. The storage unit defined in claim 23 wherein said housing is provided with a sump for holding a supply of a low-temperature liquid, said drum and said cylinder being made of a heat conductive material for facilitating a low-temperature storage of said specimens.

25. The storage unit defined in claim 16 wherein said insertion and retrieval mechanism includes a suction applicator.

26. The storage unit defined in claim 16 wherein said chamber is cylindrical and said specimens are horizontally disposed in said chamber.

27. The storage unit defined in claim 16, further comprising cooling means for maintaining said chamber at a predetermined low temperature.

28. The storage unit defined in claim 16, further comprising a computer operatively connected to said insertion and retrieval mechanism for automatically tracking the locations of specimens in said housing and for controlling the insertion and removal of specimens from said chamber.

29. A method for storing a multitude of samples, comprising:
providing a storage unit having a housing defining a storage chamber and further having a carrier disposed inside a chamber for supporting a plurality of specimens in a predetermined array;
shifting a plug member inwardly into said chamber and away from said opening;
moving said carrier to dispose a specimen receiving location on said carrier adjacent to said opening;
inserting a specimen through said opening to said location on said carrier;
depositing said specimen at said location on said carrier;
after the depositing of said specimen, relocating said plug member back to said opening; and
after relocating said plug member back to said opening, shifting said plug member outwardly into said opening to thereby close the opening.

30. The method defined in claim 29 wherein the shifting of said plug member inwardly into said chamber and away from said opening includes shifting said plug member into a seat on said carrier and further includes moving said carrier to relocate the shifted plug member away from said opening, the relocating of said plug member including again moving said carrier to relocate said plug member back to said opening and to simultaneously transfer the deposited specimen away from said opening.

31. The method defined in claim 29 wherein the shifting of said plug member includes operating an insertion and retrieval mechanism, the inserting and depositing of said specimen also including the operating of said insertion and retrieval mechanism.

32. The method defined in claim 29 wherein the shifting of said plug member includes operating a suction device.

33. The method defined in claim 29 wherein the inserting of said specimen includes operating a suction device.

34. The method defined in claim 29 wherein said carrier is rotatably mounted to said housing for rotation about a vertical axis, said location being one of a multiplicity of locations disposed in a cylindrical array on said carrier, the moving of said carrier including rotating said carrier about said axis.

35. The method defined in claim 29, further comprising cooling said chamber to a low temperature.

36. The method defined in claim 29, further comprising operating a computer to automatically track the locations of specimens in said housing and for controlling the insertion and removal of specimens from said chamber.

37. A storage unit comprising:
a housing defining a storage chamber, said housing having a sidewall;
a carrier disposed inside said chamber for supporting a plurality of specimens in a predetermined cylindrical array;
a drive operatively connected to said carrier for rotating said carrier about a vertical axis;
an access port on said sidewall for enabling lateral access to said chamber for insertion and retrieval of specimens from said carrier, said access port including an opening in said sidewall and further including a plug member removably located in said opening, said sidewall being provided with a magnetic retainer for cooperating with said plug member to hold said plug member in said opening, said plug member being provided with magnetic elements; and
an insertion and removal mechanism coupled to said housing for alternately inserting and removing specimens from said chamber via said access port.

38. A storage unit comprising:
a housing defining a storage chamber, said housing having a sidewall, said housing being provided with a sump for holding a supply of a low-temperature liquid;
a carrier disposed inside said chamber for supporting a plurality of specimens in a predetermined cylindrical array;
a drive operatively connected to said carrier for rotating said carrier about a vertical axis;
an access port on said sidewall for enabling lateral access to said chamber for insertion and retrieval of specimens from said carrier, said access port including an opening in said sidewall and further including a plug member removably located in said opening, said plug member having a fit in said opening enabling pressure release; and
an insertion and removal mechanism coupled to said housing for alternately inserting and removing specimens from said chamber via said access port.

39. A storage unit comprising:
a dewar-type housing defining a storage chamber, said housing having a dewar-type sidewall;
a carrier rotatably disposed inside said chamber for supporting a plurality of specimens in a predetermined cylindrical array;
a drive operatively connected to said carrier for rotating said carrier about a vertical axis;
an access port penetrating through said sidewall for enabling lateral access to said chamber for insertion and retrieval of specimens from said carrier; and
an insertion and removal mechanism coupled to said housing for alternately inserting and removing specimens from said chamber via said access port.

40. The storage unit defined in claim 39 wherein said access port includes an elongate vertically extending slot in said sidewall and further includes an elongate plug member removably located in said slot.

41. The storage unit defined in claim 39 wherein said sidewall is provided with retainer for cooperating with said plug member to hold said plug member in said slot.

42. The storage unit defined in claim 41 wherein said retainer is magnetic, said plug member being provided with magnetic elements.

43. A storage unit comprising:

a dewar-type housing defining a storage chamber, said housing having a dewar-type sidewall;

a carrier disposed inside said chamber for supporting a plurality of specimens in a predetermined cylindrical array;

an access port penetrating through said sidewall for enabling lateral access to said chamber for insertion and retrieval of specimens from said carrier;

an insertion and removal mechanism coupled to said housing for alternately inserting and removing specimens from said chamber via said access port; and a sump in said housing holding a supply of a low-temperature liquid, said carrier being spaced from said liquid in said sump.

\* \* \* \* \*